(12) United States Patent
Zhang et al.

(10) Patent No.: US 8,962,897 B2
(45) Date of Patent: Feb. 24, 2015

(54) CATALYSTS AND PROCESSES FOR PRODUCING BUTANOL

(71) Applicant: Celanese International Corporation, Irving, TX (US)

(72) Inventors: Cheng Zhang, Houston, TX (US); Kenneth Balliet, Pasadena, TX (US); Victor J. Johnston, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/719,886

(22) Filed: Dec. 19, 2012

(65) Prior Publication Data

US 2014/0171696 A1    Jun. 19, 2014

(51) Int. Cl.

| | |
|---|---|
| *C07C 27/00* | (2006.01) |
| *C07C 29/00* | (2006.01) |
| *B01J 23/00* | (2006.01) |
| *B01J 23/02* | (2006.01) |
| *B01J 23/08* | (2006.01) |
| *B01J 23/40* | (2006.01) |
| *B01J 23/42* | (2006.01) |
| *B01J 23/44* | (2006.01) |
| *B01J 23/56* | (2006.01) |
| *B01J 23/72* | (2006.01) |
| *B01J 21/04* | (2006.01) |
| *B01J 20/00* | (2006.01) |
| *C07C 29/34* | (2006.01) |
| *B01J 23/14* | (2006.01) |
| *B01J 23/62* | (2006.01) |
| *B01J 23/75* | (2006.01) |
| *B01J 27/24* | (2006.01) |
| *B01J 37/08* | (2006.01) |
| *B01J 21/06* | (2006.01) |
| *B01J 23/06* | (2006.01) |
| *B01J 23/745* | (2006.01) |
| *B01J 23/755* | (2006.01) |
| *B01J 37/02* | (2006.01) |
| *B01J 21/10* | (2006.01) |
| *B01J 35/02* | (2006.01) |
| *B01J 37/00* | (2006.01) |

(52) U.S. Cl.
CPC .................. *C07C 29/34* (2013.01); *B01J 23/14* (2013.01); *B01J 23/42* (2013.01); *B01J 23/44* (2013.01); *B01J 23/626* (2013.01); *B01J 23/72* (2013.01); *B01J 23/75* (2013.01); *B01J 27/24* (2013.01); *B01J 37/08* (2013.01); *B01J 21/04* (2013.01); *B01J 21/066* (2013.01); *B01J 23/06* (2013.01); *B01J 23/745* (2013.01); *B01J 23/755* (2013.01); *B01J 37/0201* (2013.01); *B01J 37/0203* (2013.01); *B01J 37/0207* (2013.01); *B01J 21/063* (2013.01); *B01J 21/10* (2013.01); *B01J 35/023* (2013.01); *B01J 37/0018* (2013.01)
USPC ........... 568/905; 502/327; 502/331; 502/332; 502/333; 502/339; 502/345; 502/346; 502/349; 502/355; 502/439

(58) Field of Classification Search
CPC .......... B01J 21/00; B01J 21/04; B01J 21/063; B01J 21/066; B01J 21/10; B01J 23/06; B01J 23/14; B01J 23/40; B01J 23/42; B01J 23/44; B01J 23/58; B01J 23/60; B01J 23/70; B01J 23/72; B01J 23/74; B01J 23/745; B01J 23/75; B01J 23/755; B01J 23/78; B01J 23/80; B01J 23/89; B01J 23/8946; B01J 23/8953; B01J 23/8966; B01J 29/0316; B01J 29/0352; B01J 29/042; B01J 29/064
USPC ......... 502/66, 73, 74, 87, 326–346, 349–351, 502/355, 415, 439; 568/905
See application file for complete search history.

(56) References Cited

U.S. PATENT DOCUMENTS

| | | | |
|---|---|---|---|
| 1,992,480 | A | 2/1935 | Otto et al. |
| 2,762,847 | A | 9/1956 | Miller et al. |
| 3,864,407 | A | 2/1975 | Yates |
| 4,011,273 | A | 3/1977 | Abend et al. |
| 4,518,810 | A | 5/1985 | Matsuda et al. |
| 4,533,775 | A | 8/1985 | Fox et al. |
| 4,551,444 | A | 11/1985 | Lin et al. |
| 5,095,156 | A | 3/1992 | Radlowski et al. |
| 5,159,125 | A | 10/1992 | Hagen |

(Continued)

FOREIGN PATENT DOCUMENTS

| | | |
|---|---|---|
| CN | 1528727 | 9/2004 |
| CN | 101530802 | 9/2009 |

(Continued)

OTHER PUBLICATIONS

OXO Alcohols, Process Economics Program Report 21E, Sep. 2010 (203 pages).
Matsu-ura, et al., Journal of Organic Chemistry, vol. 71, No. 21, pp. 8306-8308.
Dvornikoff, et al., Journal of Organic Chemistry, 1957, 11, pp. 540-542.
Carlini, et al., Journal of Molecular Catalysis A: Chemical, vol. 212, 2004, pp. 65-70.
DiCosimo, et al., Journal of Catalysis, vol. 190, 2000, pp. 261-275.
International Search Report and Written Opinion for PCT/US2013/076036 mailed Apr. 16, 2014.

*Primary Examiner* — Cam N. Nguyen

(57) ABSTRACT

In one embodiment, the invention is to a catalyst composition for converting ethanol to higher alcohols, such as butanol. The catalyst composition comprises one or more metals and one or more supports. The one or more metals selected from the group consisting of cobalt, nickel, palladium, platinum, zinc, iron, tin and copper. The one or more supports are selected from the group consisting of $Al_2O_3$, $ZrO_2$, MgO, $TiO_2$, zeolite, ZnO, and mixtures thereof, wherein the catalyst is substantially free of alkali metals and alkaline earth metals.

20 Claims, No Drawings

(56) References Cited

U.S. PATENT DOCUMENTS

| | | | |
|---|---|---|---|
| 5,217,938 A * | 6/1993 | Reinalda et al. | 502/325 |
| 5,300,695 A | 4/1994 | Radlowski | |
| 5,849,662 A * | 12/1998 | Praserthdam | 502/330 |
| 6,166,265 A | 12/2000 | Kanand et al. | |
| 6,218,326 B1 | 4/2001 | Datta et al. | |
| 6,265,342 B1 * | 7/2001 | Lim et al. | 502/326 |
| 6,323,383 B1 | 11/2001 | Tsuchida et al. | |
| 6,429,168 B1 * | 8/2002 | Vernooy | 502/331 |
| 7,314,960 B1 | 1/2008 | Lin et al. | |
| 7,700,810 B2 | 4/2010 | Kourtakis et al. | |
| 7,700,811 B2 | 4/2010 | Kourtakis et al. | |
| 7,700,812 B2 | 4/2010 | Kourtakis et al. | |
| 7,700,813 B2 | 4/2010 | Kourtakis et al. | |
| 7,705,192 B2 | 4/2010 | Kourtakis et al. | |
| 7,807,857 B2 | 10/2010 | Kourtakis et al. | |
| 7,838,710 B2 * | 11/2010 | Ryu | 585/274 |
| 7,915,196 B2 * | 3/2011 | Parent et al. | 502/335 |
| 8,071,822 B2 | 12/2011 | Ozer et al. | |
| 8,071,823 B2 | 12/2011 | Ozer et al. | |
| 8,232,433 B2 | 7/2012 | Onda et al. | |
| 8,337,791 B2 * | 12/2012 | Kohara et al. | 423/213.2 |
| 8,466,082 B2 * | 6/2013 | Hagemeyer et al. | 502/242 |
| 8,476,321 B2 * | 7/2013 | Baijense | 518/715 |
| 8,569,203 B2 * | 10/2013 | Weiner et al. | 502/349 |
| 8,586,780 B2 * | 11/2013 | Hagemeyer et al. | 560/247 |
| 8,604,248 B2 * | 12/2013 | King et al. | 564/470 |
| 8,680,005 B2 * | 3/2014 | Hannemann et al. | 502/339 |
| 2007/0255079 A1 | 11/2007 | Tsuchida et al. | |
| 2009/0056204 A1 | 3/2009 | Tsuchida et al. | |
| 2010/0160692 A1 | 6/2010 | Kourtakis et al. | |
| 2010/0185021 A1 | 7/2010 | Ross et al. | |
| 2010/0205857 A1 | 8/2010 | Dijk et al. | |
| 2010/0298613 A1 | 11/2010 | Tanaka et al. | |
| 2011/0236302 A1 * | 9/2011 | Hanakata et al. | 423/651 |
| 2011/0257443 A1 * | 10/2011 | Weiner et al. | 568/885 |
| 2011/0288344 A1 | 11/2011 | Grady et al. | |
| 2011/0318932 A1 * | 12/2011 | Monson et al. | 438/706 |
| 2012/0040427 A1 | 2/2012 | Bell et al. | |
| 2013/0131399 A1 * | 5/2013 | Weiner et al. | 568/885 |
| 2013/0165700 A1 * | 6/2013 | Zhou et al. | 568/885 |
| 2013/0165701 A1 * | 6/2013 | Zhou et al. | 568/885 |
| 2013/0165703 A1 * | 6/2013 | Weiner et al. | 568/885 |
| 2013/0178662 A1 * | 7/2013 | Zhou et al. | 568/885 |
| 2013/0178666 A1 * | 7/2013 | Zhou et al. | 568/885 |
| 2013/0178668 A1 * | 7/2013 | Zhou et al. | 568/885 |
| 2013/0178669 A1 * | 7/2013 | Zhou et al. | 568/885 |
| 2013/0184502 A1 * | 7/2013 | Zhou et al. | 568/885 |
| 2013/0211150 A1 * | 8/2013 | Zhou et al. | 568/885 |
| 2013/0224090 A1 * | 8/2013 | Lee et al. | 423/213.5 |
| 2013/0225878 A1 * | 8/2013 | Weiner et al. | 568/885 |
| 2013/0245332 A1 * | 9/2013 | Weiner et al. | 568/885 |

FOREIGN PATENT DOCUMENTS

| | | |
|---|---|---|
| WO | WO 2006/059729 | 6/2006 |
| WO | WO 2009/097310 | 8/2009 |
| WO | WO 2009/097312 | 9/2009 |

* cited by examiner

CATALYSTS AND PROCESSES FOR PRODUCING BUTANOL

FIELD OF THE INVENTION

The present invention relates generally to a process of making higher molecular weight alcohols from ethanol and, in particular, to a catalytic conversion of ethanol to butanol.

BACKGROUND OF THE INVENTION

Studies have been done for economically viable processes to produce butanol. Like ethanol, butanol may be a possible solution to dependency on oil as both may be used as a fuel in an internal combustion engine. In fact, due to the longer hydrocarbon chain and non-polar characteristics, butanol may be a better fuel option than ethanol because butanol is more similar to gasoline than ethanol. In addition, butanol may be used in the manufacture of pharmaceuticals, polymers, pyroxylin plastics, herbicide esters and butyl xanthate. Butanol may also be used as a solvent for the extraction of essential oils or as an ingredient in perfumes; as an extractant in the manufacture of antibiotics, hormones, and vitamins; as a solvent for paints, coatings, natural resins, gums, synthetic resins, alkaloids, and camphor. Other applications of butanol includes as swelling agent in textiles; as a component of break fluids, cleaning formulations, degreasers, and repellents; and as a component of ore floatation agents and of wood-treating systems.

Butanol is typically produced industrially from petrochemical feedstock propylene in the presence of a rhodium-based homogeneous catalyst. During this process, propylene is hydroformylated to butyraldehyde and butyraldehyde is then hydrogenated to product butanol. However, due to the fluctuating natural gas and crude oil prices the cost of producing butanol using this method also becomes more unpredictable and significant.

It is known that butanol may be prepared by condensation from ethanol over basic catalyst at high temperature using the Guerbet reaction. The reaction mechanism for the conversion of ethanol to butanol via the Guerbet reaction comprises a four-step sequence as shown in reaction scheme 1. In the first step, ethanol is oxidized to intermediate aldehyde and two of the intermediate aldehydes undergo an aldol condensation reaction to form crotonaldehyde, which is reduced to butanol via hydrogenation. See, for example, J. Logsdon in *Kirk-othmer Encyclopedia of Chemical Technology*, John Wiley and Sons, Inc., New York, 2001; *J. Mol. Catal. A: Chem.*, 2004, 212, p. 65; and *J Org. Chem.*, 2006, 71, p. 8306.

Various catalysts have been studied to improve the conversion and selectivity of ethanol to butanol. For example, M. N. Dvornikoff and M. W. Farrar, J. of Organic Chemistry (1957), 11, 540-542, discloses the use of a MgO—$K_2CO_3$—$CuCrO_2$ catalyst system to promote ethanol condensation to higher alcohols, including butanol. U.S. Pat. No. 5,300,695 discloses processes where an L-type zeolite catalyst, such as potassium L-type zeolite, is used to react with an alcohol having X carbon atoms to produce alcohol with higher molecular weight.

The use of hydroxyapatite $Ca_{10}(PO_4)_6(OH)_2$, tricalcium phosphate $Ca_3(PO_4)_2$, calcium monohydrogen phosphate $CaHPO_4.(0-2)H_2O$, calcium diphosphate $Ca_2P_2O_7$, octacalcium phosphate $Ca_8H_2(PO_4)_6.5H_2O$, tetracalcium phosphate $Ca_4(PO_4)_2O$, or amorphous calcium phosphate $Ca_3(PO_4)_2.nH_2O$, to convert ethanol to higher molecular weight alcohols are disclosed in WO2006059729.

Carlini et al., Carlini et al., Journal of Molecular Catalysis A: Chemical (2005), 232, 13-20, discloses bifunctional heterogeneous hydrotalcites for converting methanol and n-propanol to isobutyl alcohol.

Others catalyst systems for making higher molecular weight alcohols from methanol or ethanol have also been studied. For example, U.S. Pat. No. 4,551,444 discusses the use of multi-component catalyst system using various metals; U.S. Pat. No. 5,095,156 and U.S. Pat. No. 5,159,125 discusses the impact of magnesium oxide; U.S. Pat. No. 4,011,273 discusses the use of insoluble lead catalysts; U.S. Pat. No. 7,807,857 focuses on Group II metal salts; and U.S. Pat. No. 4,533,775 discusses a catalyst system comprising a metal acetylide, a hydride, an alkoxide and promoter.

The references mentioned above are hereby incorporated by reference.

Nonetheless, the need remains for improved catalysts for making butanol from ethanol, especially those having improved activity and selectivity to butanol.

SUMMARY OF THE INVENTION

In a first embodiment, the present invention is directed to a catalyst for converting alcohols to higher alcohols. The catalyst comprises one or more metals and one or more supports. Preferably, one or more metals selected from the group consisting of cobalt, nickel, palladium, platinum, iron, zinc, tin and copper. Preferably, the one or more supports are selected from the group consisting of $Al_2O_3$, $ZrO_2$, MgO, $TiO_2$, zeolite, ZnO, and a mixture thereof.

In a second embodiment, the present invention is directed to a catalyst for converting alcohols to higher alcohols. The Scheme 1

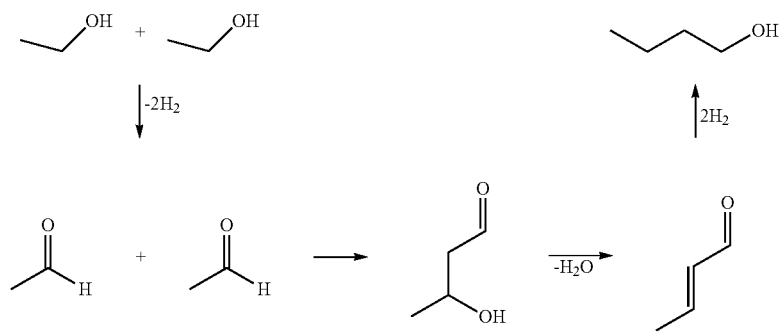

catalyst comprises one or more support and one or more metal layers on the one or more supports. Preferably, the one or more supports are selected from the group consisting of $Al_2O_3$, $ZrO_2$, MgO, $TiO_2$, zeolite, ZnO, and a mixture thereof. Preferably, the metal layer on the one or more supports comprise one or more metals selected from the group consisting of cobalt, nickel, palladium, platinum, iron, zinc, tin and copper.

In a third embodiment, the present invention is directed to a process for producing butanol. The process comprises the step of feeding a gaseous stream comprising ethanol over a catalyst in a reactor to form butanol wherein the catalyst comprises one or more metals and one or more supports. Preferably, the one or more metals are selected from the group consisting of cobalt, nickel, palladium, platinum, iron, zinc, tin and copper. Preferably, the one or more supports are selected from the group consisting of $Al_2O_3$, $ZrO_2$, MgO, $TiO_2$, zeolite, ZnO, and a mixture thereof.

DETAILED DESCRIPTION OF THE INVENTION

Introduction

The present invention generally relates to a process for synthesizing a linear multi-carbon alcohol from an alcohol having two or fewer carbons that is useful as a chemical industry raw material and fuel composition or a mixture thereof.

Production of multi-carbon alcohols, like butanol, using most conventional processes has been limited by economic and environmental constraints. One of the best known processes is the Guerbet reaction. Specifically, ethanol may be used as the starting material to product butanol. However, intermediates of the reaction can form competing by-products, such as diethyl ether, ethylene, 1-hexanol, 2-ethylbutanol, and/or 2-ethylhexanol. These intermediates may lead to impurities in the butanol product. For example, diethyl ether and ethylene may be formed due to the dehydration of ethanol in the presence of an acidic catalyst. 1-hexanol may also be formed via the addition of aldehyde to butyraldehyde, a crotonaldehyde intermediate. Butyraldehyde may also react with other intermediates to form 2-ethylbutanol and 2-ethylhexanol. A crude mixture of the multi-carbon alcohol and impurities may increase the purification needed to recover butanol.

Catalysts, such as multi-catalyst systems, hydroxyapatite, and phosphate derivatives have been used to optimize the yields and selectivity to butanol. In addition, process conditions for the Guerbet reaction have also been studied to optimize the yields and selectivity to butanol.

The Guerbet reaction converts two moles of ethanol to one mole of butanol through multiple intermediates. The reaction comprising first oxidizing ethanol to form an aldehyde, condensing the aldehydes to 3-hydroxy-butyraldehyde, dehydrating the 3-hydroxy-butyraldehyde to crotonaldehyde, and reducing the crotonaldehyde to butanol.

It has now been discovered that certain catalysts effectively oxidizes ethanol to form an intermediate aldehyde, which forms crotonaldehyde, and reduces crotonaldehyde to butanol. Preferably, the catalysts of the present invention serve as a base to oxidize ethanol and to promote aldol condensation, and also as a hydrogenating site for crotonaldehyde to form butanol. Surprisingly and unexpectedly, the inventors found that a catalyst system of at least one metal coated on a support beneficially results in the improvement of ethanol conversion, and/or butanol selectivity. Moreover, the novel catalyst system beneficially reduces the selectivities to DEE and ethylene. For purposes of this application, linear multi-carbon alcohols are preferred and thus butanol refers to n-butanol unless otherwise indicated.

Catalyst Composition

In another embodiment, the present invention relates to a catalyst that comprises a metal selected from the group consisting of cobalt, nickel, palladium, platinum, iron, zinc, tin and copper on a support. More preferably, the metals are selected from the group consisting of palladium, copper, tin, and cobalt. The metal may be coated on the support. In one embodiment, the catalyst comprises a metal in an amount from 0.01 wt. % to 20 wt. %, e.g., from 0.05 wt. % to 18 wt. %, or from 0.1 wt. % to 16 wt. %. The supports may include those described above, preferably, $Al_2O_3$, $ZrO_2$, MgO, $TiO_2$, zeolite, ZnO, and mixtures thereof. Preferably, in this embodiment, the catalyst does not comprise an alkali metal and/or an alkaline earth metal. Thus, the catalyst may be substantially free of alkali metals and/or alkaline earth metals.

In one embodiment, the support may be $Al_2O_3$, $ZrO_2$, MgO, $TiO_2$, zeolite, ZnO, and mixtures thereof. Preferably the support is $Al_2O_3$, $ZrO_2$, or ZnO. Suitable supports may have a surface area that is at least 500 $m^2/g$, e.g., at least 200 $m^2/g$ or at least 50 $m^2/g$.

Alumina supports may include gamma-alumina ($\gamma$-$Al_2O_3$), etu-alumina ($\eta$-$Al_2O_3$), kappa alumina ($\kappa$-$Al_2O_3$), theta-alumina ($\theta$-$Al_2O_3$), or other alumina phase which is stable at temperatures use for catalyst calcination and conversion of alcohols, such as ethanol, to other alcohols, such as butanol. Unless otherwise indicated, for purposes of the present invention gamma-alumina is preferred.

Zeolite as used in the present application generally refers to microporous, aluminosilicate minerals. Examples of suitable zeolites include, but not limited to, silicoaluminophosphate (SAPO-34), clinoptilolite, ZSM-5, X-zeolite, Y-zeolite.

The amount of support may vary depending on the metal loadings and generally comprises the balance of the catalyst. In one embodiment, the catalyst comprises the support in an amount from 80 wt. % to 99.99 wt. %, e.g., from 82 wt. % to 99.95 wt. %, or from 84 wt. % to 99.9 wt. %.

In one embodiment, the catalyst may comprise copper and $\gamma$-$Al_2O_3$. The catalyst composition may comprise from 0.1 wt. % to 20 wt. % copper, e.g., from 0.5 wt. % to 18 wt. %, or from 1 wt. % to 16 wt. %. The catalyst composition comprises from 80 wt. % to 99.9 wt. % $\gamma$-$Al_2O_3$, e.g., 82 wt. % to 99.5 wt. % or from 84 wt. % to 99 wt. %.

In another embodiment, the catalyst may comprise cobalt and $\theta$-$Al_2O_3$. The catalyst composition may comprise from 0.1 wt. % to 20 wt. % cobalt, e.g., from 0.5 wt. % to 18 wt. %, or from 1 wt. % to 16 wt. %. The catalyst composition comprises from 80 wt. % to 99.9 wt. % $\theta$-$Al_2O_3$, e.g., 82 wt. % to 99.5 wt. % or from 84 wt. % to 99 wt. %.

In yet another embodiment, the catalyst may comprise copper and $ZrO_2$. The catalyst composition may comprise from 0.1 wt. % to 20 wt. % copper, e.g., from 0.5 wt. % to 18 wt. %, or from 1 wt. % to 16 wt. %. The catalyst composition comprises from 80 wt. % to 99.9 wt. % $ZrO_2$, e.g., 82 wt. % to 99.5 wt. % or from 84 wt. % to 99 wt. %.

In one embodiment, the catalysts may comprise a support coated by one metal layer that comprises one metal. The metal is selected from the group consisting of cobalt, nickel, palladium, platinum, zinc, iron, tin and copper. In a preferred embodiment, the metal is selected from the group consisting of cobalt, nickel, palladium, platinum, tin and copper.

In one embodiment, the catalyst comprises a support, a metal layer. The metal layer may be coated on the support. In one embodiment, the metal layer is a metal selected from the group consisting of cobalt, nickel, palladium, platinum, iron, zinc, tin and copper. The metal layer may be applied on the support through an impregnation process.

It has now been found that the metal-coated support catalysts surprisingly achieve unexpectedly high butanol selectivity and yield in comparison to metal-free catalysts. Furthermore, the increase of butanol selectivity and yield is accompanied by the decrease of selectivity to by-products, such as diethyl ether (DEE) and ethylene. As stated above, DEE and ethylene are made in the reaction mixture by ethanol dehydration in the presence of an acid. In one embodiment, surprisingly and unexpectedly, it has now been found that the catalysts inhibit DEE and ethylene formation. For example, the butanol selectivity of at least 20%, e.g., at least 30%, or at least 40% may be achieved with the catalyst compositions. Surprisingly and unexpectedly, this increase of butanol selectivity is accompanied by the decrease of by-products selectivities. For example, selectivity to DEE is less than 15 wt. %, e.g., less than 10 wt. %, or less than 5 wt. %. Furthermore, the ethylene selectivity is less than 10 wt. %, e.g., less than 5 wt. %, or less than 1 wt. %. In one embodiment diethyl ether and ethylene selectivity may be less than the butanol selectivity. Thus, the catalyst favors the formation of butanol. Without being bound by theory, it is postulated as a result of coating the surface of the supports with at least one metal, the catalyst composition may drive the Guerbet reaction favorably for butanol selectivity while suppressing the production of DEE and ethylene as compared to metal free support catalysts.

In one embodiment, surprisingly and unexpectedly, it has also been found that the metal-coated catalyst could also inhibit the DEE formation. In one embodiment, surprisingly and unexpectedly, it has been found that copper $\gamma$-$Al_2O_3$, copper $\theta$-$Al_2O_3$, and copper $ZrO_2$ catalysts inhibit DEE and ethylene formation. Specifically, the inventors found that the catalyst compositions enhance the selectivity of butanol by suppressing the formation of DEE and ethylene.

Water is a byproduct when converting ethanol to butanol. Since water is more polar than ethanol, it is believed that water might compete with ethanol on the polar surface of the catalyst. The inventors have found that the surface polarity of the catalysts may be modified by introducing an organic metal precursor to the surface of the support to minimize the water/ethanol competition. The organic metal precursor may include pyridine, ammonium hydroxide tetramethylammonium hydroxide, tetrabutylammonium hydroxide, methyl amine, imidazole, and other suitable support modifiers. The organic metal precursors may be support modifiers that may adjust the chemical or physical properties of the support material such as the acidity or basicity of the support material. As such, the amount and residence time of ethanol on the surface of the catalyst maybe increased and thereby promoting the carbon-carbon capillary condensation.

In other embodiments, in addition to a support, the catalyst may further comprise a support modifier. A modified support, in one embodiment, relates to a support that includes a support material and a support modifier, which, for example, may adjust the chemical or physical properties of the support material such as the acidity or basicity of the support material.

The catalyst may further comprise other additives, examples of which may include: molding assistants for enhancing moldability; reinforcements for enhancing the strength of the catalyst; pore-forming or pore modification agents for formation of appropriate pores in the catalyst, and binders. Examples of these other additives include oxalic acid, citric acid, polyacrylic acid, adipic acid, stearic acid, graphite, starch, cellulose, silica, alumina, glass fibers, silicon carbide, and silicon nitride. Preferably, these additives do not have detrimental effects on the catalytic performances, e.g., conversion and/or activity. These various additives may be added in such an amount that the physical strength of the catalyst does not readily deteriorate to such an extent that it becomes impossible to use the catalyst practically as an industrial catalyst.

In some embodiments, the catalyst composition comprises a pore modification agent, such as oxalic acid. A preferred type of pore modification agent is thermally stable and has a substantial vapor pressure at a temperature below 300° C., e.g., below 250° C. In one embodiment, the pore modification agent has a vapor pressure of at least 0.1 kPa, e.g., at least 0.5 kPa, at a temperature between 150° C. and 250° C., e.g., between 150° C. and 200° C.

The pore modification agent has a relatively high melting point, e.g., greater than 60° C., e.g., greater than 75° C., to prevent melting during the compression of the catalyst into a slug, tablet, or pellet. Preferably, the pore modification agent comprises a relatively pure material rather than a mixture. As such, lower melting components will not liquefy under compression during formation of slugs or tablets. For example, where the pore modification agent is a fatty acid, lower melting components of the fatty acid mixtures may be removed as liquids by pressing. If this phenomenon occurs during slug or tablet compression, the flow of liquid may disturb the pore structure and produce an undesirable distribution of pore volume as a function of pore diameter on the catalyst composition. In other embodiments, the pore modification agents have a significant vapor pressure at temperatures below their melting points, so that they can be removed by sublimination into a carrier gas.

Catalyst Preparation

The catalyst was synthesized using impregnation method with a metal coated the support. A support is pressed under force for a predetermined time to form pellets. For example, the support may be pressed at 180,000 N. The pellets are lightly crushed to a desired particle size. An amount of the support in pellets form is measured and placed in a round bottom reactor. A first metal is prepared by dissolving a metal precursor, such as a metal nitrate, in an amount of water and/or acetone to form a first metal precursor solution, which is impregnated on to the support by stepwise incipient wetness using the rotating dryer. The first metal coated support is dried in an oven at a desired temperature for a period of time and followed by calcination.

The initial temperature may range from 10° C. to 150° C., e.g., 30° C. to 120° C., or 50° C. to 90° C. The temperature ramping rate may be from 1° C. to 5° C. per minute. The final temperature may vary depending on the catalyst composition and generally ranges from 300° C. to 900° C., e.g., from 450° C. to 800° C., or from 500° C. to 700° C. The holding time is between 1 hour and 10 hours, e.g., between 2 hours and 8 hours, or between 4 hours and 6 hours. Depending on the metal used, other temperature profiles may be suitable. The calcination of the mixture may be done in an inert atmosphere, air or an oxygen-containing gas at the desired temperatures. Steam, a hydrocarbon or other gases or vapors may be added to the atmosphere during the calcination step or post-calcination to cause desired effects on physical and chemical surface properties as well as textural properties such as increase macroporosity.

As an example, the temperature profile may start at 60° C., increase at a rate of 5° C. per minute until the temperature reaches 600° C., and hold at 600° C. for 5 hours, and cooling to room temperature. For Group VIII metals, the calcination temperature may be lower, such as 300° C.

In an embodiment, any suitable metal precursors may be used to make the catalyst composition. Non-limiting examples of suitable metal precursors include metal oxides, metal hydroxides (including hydrated oxides), metal salts of inorganic and organic acids such as, e.g., nitrates, nitrites, sulfates, halides (e.g., fluorides, chlorides, bromides and iodides), carbonates, phosphates, azides, borates (including fluoroborates, pyrazolylborates, etc.), sulfonates, carboxylates (such as, e.g., formates, acetates, propionates, oxalates and citrates), substituted carboxylates (including halogenocarboxylates such as, e.g., trifluoroacetates, hydroxycarboxylates, aminocarboxylates, etc.) and salts and acids wherein the metal is part of an anion (such as, e.g., hexachloroplatinates, tetrachloroaurate, tungstates and the corresponding acids).

Further non-limiting examples of suitable metal precursors for the processes of the present invention include alkoxides, complex compounds (e.g., complex salts) of metals such as, e.g., beta-diketonates (e.g., acetylacetonates), complexes with amines, N-heterocyclic compounds (e.g., pyrrole, aziridine, indole, piperidine, morpholine, pyridine, imidazole, piperazine, triazoles, and substituted derivatives thereof), aminoalcohols (e.g., ethanolamine, etc.), amino acids (e.g., glycine, etc.), amides (e.g., formamides, acetamides, etc.), and nitriles (e.g., acetonitrile, etc.). Non-limiting examples of preferred metal precursors include nitrates and oxides.

Non-limiting examples of specific metal precursors for use in the processes of the present invention include palladium bromide, palladium chloride, palladium iodide, palladium nitrate, palladium nitrate hydrate, tetraamine palladium nitrate, palladium oxide, palladium oxide hydrate, and palladium sulfate; copper oxide, copper hydroxide, copper nitrate, copper sulfate, copper chloride, copper formate, copper acetate, copper neodecanoate, copper ethylhexanoate, copper methacrylate, copper trifluoroacetate, copper acetoacetate and copper hexafluoroacetylacetonate; and cobalt acetate, cobalt hydroxide, cobalt carbonate, cobalt nitrate, cobalt 2,4-pentaedionate, cobalt formate, cobalt oxide, cobalt chloride, cobalt alkoxide, cobalt perchlorate, and cobalt carboxylate. The above compounds may be employed as such or optionally in the form of solvates and the like such as, e.g., as hydrates. Examples of specific metal precursors that may be used in the present invention include palladium nitrate hydrate, copper nitrate hydrate, and cobalt nitrate.

The use of mixtures of different compounds, e.g., different salts, of the same metal and/or the use of mixtures of compounds of different metals and/or of mixed metal precursors (e.g., mixed salts and/or mixed oxides) is also contemplated by the present invention. Provided that none of the different metals comprise alkali or alkaline earth metals. Accordingly, the term "metal precursor" as used herein includes both a single metal precursor and any mixture of two or more metal precursors. In a preferred embodiment, the catalyst composition is made using at least one metal and a support.

Production of Butanol

Suitable reactions and/or separation scheme may be employed to form a crude product stream comprising butanol using the catalysts. For example, in some embodiments, the crude product stream is formed by contacting a low molecular weight alcohol, e.g., ethanol, with the catalysts to form the crude higher alcohol product stream, i.e., a stream with butanol. The catalyst may also be a metal on a support. In a preferred embodiment, the crude product stream is the reaction product of the condensation reaction of ethanol, which is conducted over a metal-coated support. In one embodiment, the crude product stream is the product of a vapor phase reaction.

The feedstream may be a gaseous stream comprising ethanol. Preferably, the gaseous stream comprise more than 5 vol. % ethanol, e.g., more than 10 vol. % or more than 20 vol. %. The feedstream may also comprise other molecules such as pyridine, $NH_3$ and alkyl amine. Inert gases may be in the gaseous stream and thus may include nitrogen, helium, argon, and methane. Preferably, no hydrogen is introduced with the gaseous stream, and thus the gaseous stream is substantially free of hydrogen. Without being bound by theory the hydrogen needed for the intermediate reactions may be produced in situ.

In some embodiments, the condensation reaction may achieve favorable conversion of ethanol and favorable selectivity and productivity to butanol. For purposes of the present invention, the term "conversion" refers to the amount of ethanol in the feed that is converted to a compound other than ethanol. Conversion is expressed as a percentage based on ethanol in the feed. The conversion of ethanol may be at least 20%, e.g., at least 30%, at least 40%, or at least 50%.

Selectivity, as it refers to the formation of butanol, is expressed as the ratio of the amount of carbon in the desired product(s) and the amount of carbon in the total products. This ratio may be multiplied by 100 to arrive at the selectivity. Preferably, the selectivity to butanol is at least 20%, e.g., at least 30%, or at least 40%. In some embodiments, the catalyst selectivity to $C_{4+}$ alcohols, e.g., butanol, isobutanol, 2-butanol, tert-butanol, 1-hexanol, 2-ethylbutanol, and 2-ethylhexanol, is at least 30%, e.g., at least 50%, at least 60%, or at least 80%.

Preferred embodiments of the process demonstrate a low selectivity to undesirable products, such as diethyl ether and ethylene. The selectivity to these undesirable products preferably is less than 20%, e.g., less than 5% or less than 1%. More preferably, these undesirable products are not detectable.

The ethanol may be fed to the reactor as a liquid stream or a vapor stream. Preferably, the ethanol is fed as a vapor stream. The reactor may be any suitable reactor or combination of reactors. Preferably, the reactor comprises a fixed bed reactor or a series of fixed bed reactors. In one embodiment, the reactor is a gas flow catalytic reactor or a series of gas flow catalytic reactors. Of course, other reactors such as a continuous stirred tank reactor or a fluidized bed reactor may be employed. In one embodiment, the vapor ethanol stream is substantially free of hydrogen, e.g., less than 1 wt. % hydrogen, less than 0.1 wt. %, or less than 0.01 wt. %.

The condensation reaction may be conducted at a temperature of at least 200° C., e.g., at least 300° C., or at least 350° C. In terms of ranges, the reaction temperature may range from 200° C. to 500° C., e.g., from 250° C. to 400° C., or from 250° C. to 350° C. Reaction time may range from 0.01 to 100 hours, e.g., from 1 to 80 hours, or from 5 to 80 hours. Reaction pressure is not particularly limited, and the reaction is typically performed near atmospheric pressure. In one embodiment, the reaction may be conducted at a pressure ranging from 0.1 kPa to 9,000 kPa, e.g., from 20 kPa to 5,000 kPa, or from 90 to 3500 kPa. The ethanol conversion may vary depending upon the reaction temperature and/or pressure.

In one embodiment, the reaction is conducted at a gas hourly space velocity ("GHSV") greater than 600 $hr^{-1}$, e.g., greater than 1,000 $hr^{-1}$ or greater than 2,000 $hr^{-1}$. The GHSV range from 600 $hr^{-1}$ to 10,000 $hr^{-1}$, e.g., from 1,000 $hr^{-1}$ to 8,000 $hr^{-1}$ or from 1,500 $hr^{-1}$ to 7,500 $hr^{-1}$.

An inert or reactive gas may be supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors. The addition of these additional components may improve reaction efficiencies.

In one embodiment, the unreacted components such as the ethanol as well as the inert or reactive gases that remain are recycled to the reactor after sufficient separation from the desired product.

EXAMPLES

Example 1

3 wt. % Copper γ-Aluminum Oxide

The catalyst was synthesized using impregnation method. γ-Aluminum oxide was crushed to particle size of 0.85 mm and 1.18 mm. 10 g of the above crushed γ-aluminum oxide was placed in a round bottom reactor. 1.09 g of copper nitrate hydrate was dissolved in 5 g of water, followed by impregnating to the above γ-aluminum oxide by stepwise incipient wetness using a rotating dryer. The copper-coated γ-aluminum oxide was dried in an oven at 120° C. for 5 hours, followed by calcination using the following temperature program: start at 60° C., ramp to 350° C. at 2° C./min, hold at 350° C. for 5 hours, followed by cooling to room temperature.

Example 2

3 wt. % Cobalt θ-Aluminum Oxide

The catalyst was synthesized using impregnation method. θ-Aluminum oxide was crushed to particle size of 0.85 mm and 1.18 mm. 10 g of the above crushed θ-aluminum oxide was placed in a round bottom reactor. 1.53 g of cobalt nitrate hydrate was dissolved in 5 g of water, followed by impregnating to the above θ-aluminum oxide by stepwise incipient wetness using a rotating dryer. The cobalt-coated θ-aluminum oxide was dried in an oven at 120° C. for 5 hours, followed by calcination using the following temperature program: start at 60° C., ramp to 500° C. at 2° C./min, hold at 500° C. for 5 hours, followed by cooling to room temperature.

Example 3

3 wt. % Copper Zirconium Oxide

The catalyst was synthesized using impregnation method. Zirconium oxide was crushed to particle size of 0.85 mm and 1.18 mm. 10 g of the above crushed zirconium oxide was placed in a round bottom reactor. 1.09 g of copper nitrate hydrate was dissolved in 5 g of water, followed by impregnating to the above zirconium oxide by stepwise incipient wetness using a rotating dryer. The copper-coated zirconium oxide was dried and calcined under the conditions in Example 1.

Example 4

3 wt. % Palladium Zirconium Oxide

The catalyst was synthesized using impregnation method. 10 g of the above crushed zirconium oxide (0.85 mm and 1.18 mm) was placed in a round bottom reactor. 0.3 g of palladium nitrate hydrate was dissolved in 5 g of water, followed by impregnating to the above zirconium oxide by stepwise incipient wetness using a rotating dryer. The palladium-coated zirconium oxide was dried and calcined under the conditions in Example 1.

Example 5

3 wt. % Platinum Zirconium Oxide

The catalyst was synthesized using impregnation method. 10 g of the above crushed zirconium oxide (0.85 mm and 1.18 mm) was placed in a round bottom reactor. 0.3 g of tetraammineplatinum(II) nitrate was dissolved in 5 g of water, followed by impregnating to the above zirconium oxide by stepwise incipient wetness using a rotating dryer. The platinum-coated zirconium oxide was dried and calcined under the conditions in Example 1.

Example 6

3 wt. % Tin Zirconium Oxide

The catalyst was synthesized using impregnation method. 10 g of the above crushed zirconium oxide (0.85 mm and 1.18 mm) was placed in a round bottom reactor. 0.3 g of tin oxalate was dissolved in 5 g of water, followed by impregnating to the above zirconium oxide by stepwise incipient wetness using a rotating dryer. The tin-coated zirconium oxide was dried and calcined under the conditions in Example 1.

Example 7

3 wt. % Palladium Platinum Tin Zirconium Oxide

The catalyst was synthesized using impregnation method. 10 g of the above crushed zirconium oxide (0.85 mm and 1.18 mm) was placed in a round bottom reactor. 0.56 g of tin oxalate and 0.54 g of ammonium oxalate was dissolved in 10 ml of water. 0.3 g of palladium nitrate hydrate, tetraammineplatinum(II) nitrate, was added to the tin oxalate solution, followed by impregnating to the above zirconium oxide by stepwise incipient wetness using a rotating dryer. The metal-coated zirconium oxide was dried and calcined under the conditions in Example 1.

Example 8

Catalysts were prepared and evaluated. γ-Aluminum oxide, θ-aluminum oxide, zirconium oxide without any metal coating were evaluated under the same testing conditions to serve as control. A fixed bed gas flow catalytic reactor was used as a reactor. 3 ml of the catalysts was filled in a stainless steel tube reactor with a diameter of 0.95 cm. As a pretreatment, hydrogen reduction was conducted for 1 hour under a carrier gas atmosphere (10% $H_2/N_2$ base; flow rate 125 ml/min) at 400° C. After the pretreatment, the testing was conducted at a temperature between 250° C. and 325° C. and pressure between 1 kPa and 5,100 kPa, nitrogen flow rate was at 125 sccm and ethanol flow rate was at 0.2 ml/min. The reaction duration ranges from 5 hours to 80 hours.

The ethanol conversion, butanol product selectivity, butanol yield, and $C_{4+}$ alcohol selectivity for catalyst metal-coated γ-aluminum oxide and θ-aluminum oxide as reference are shown below in Tables 1 to 3.

TABLE 1

| | Testing condition: 290° C. and 3,400 kPa | | | | | |
|---|---|---|---|---|---|---|
| Catalysts | Ethanol Conversion (%) | Butanol Selectivity (%) | Yield (%) | C$_{4+}$ Alcohols Selectivity (%) | DEE Selectivity (%) | Ethylene Selectivity (%) |
| γ-Al$_2$O$_3$ | 61 | 0 | 0 | 0 | 96 | 7 |
| Example 1 | 74 | 29 | 21 | 45 | 13 | 1 |

As shown in Table 1, γ-aluminum oxide has an ethanol conversion of 61%, but has a 0% butanol selectivity, butanol yield, C$_{4+}$ alcohol selectivity. The DEE selectivity is 96% DEE. By coating γ-aluminum oxide with copper, the butanol selectivity, butanol yield, and C$_{4+}$ alcohols selectivity increased significantly while the DEE and ethylene selectivity are suppressed.

TABLE 2

| | Testing condition: 250° C. and 3,400 kPa | | | | | |
|---|---|---|---|---|---|---|
| Catalysts | Ethanol Conversion (%) | Butanol Selectivity (%) | Yield (%) | C$_{4+}$ Alcohols Selectivity (%) | DEE Selectivity (%) | Ethylene Selectivity (%) |
| θ-Al$_2$O$_3$ | 94 | 0 | 0 | 0 | 72 | 10 |
| Example 2 | 54 | 54 | 29 | 73 | 7 | 1 |

As shown in Table 2, θ-aluminum oxide has an ethanol conversion of 94%, but has 0% butanol selectivity, butanol yield, C$_{4+}$ alcohol selectivity. The DEE selectivity is at 72%. By coating θ-aluminum oxide with cobalt, the butanol selectivity, butanol yield, and C$_{4+}$ alcohols selectivity increased significantly while the DEE and ethylene selectivity are suppressed.

TABLE 3

| | Testing condition: 360° C. and 3,400 kPa | | | | | |
|---|---|---|---|---|---|---|
| Catalysts | Ethanol Conversion (%) | Butanol Selectivity (%) | Yield (%) | C$_{4+}$ Alcohols Selectivity (%) | DEE Selectivity (%) | Ethylene Selectivity (%) |
| ZrO$_2$ | 21 | 14 | 3 | 20 | 30 | 34 |
| Example 3 | 79 | 19 | 15 | 28 | 1 | 1 |
| Example 4 | 78 | 51 | 40 | 73 | 4 | 1 |
| Example 5 | 61 | 40 | 24 | 52 | 0 | 6 |
| Example 6 | 36 | 36 | 13 | 54 | 15 | 10 |
| Example 7 | 58 | 42 | 25 | 60 | 6 | 5 |

As shown in Table 3, the copper coated zirconium oxide, palladium coated zirconium oxide, platinum coated zirconium oxide, tin coated zirconium oxide, and palladium/platinum/tin coated zirconium oxide have better ethanol conversion, butanol selectivity, butanol yield, C$_{4+}$ alcohols selectivity, and lower DEE and ethyl selectivity than the metal free zirconium oxide. Specifically, copper coated zirconium oxide has a high ethanol conversion of 79% and a low DEE and ethylene selectivity of 1% each. Similarly, palladium coated zirconium oxide has a high ethanol conversion of 78% and a low DEE and ethylene selectivity of 4% and 1%, respectively. In addition, palladium coated zirconium oxide has a high C$_{4+}$ alcohols selectivity of 73%. In addition, platinum coated zirconium oxide has an ethanol conversion of 61%, a 0% DEE selectivity, and 6% ethylene selectivity. Similarly, the palladium/platinum/tin coated zirconium has an ethanol conversion of 58%, a butanol selectivity of 42%, a butanol yield of 25%, a C$_{4+}$ alcohols selectivity of 60%, and a low DEE selectivity of 6% and a low ethylene selectivity of 5%. Therefore, coating of zirconium oxide with one or more metals increases the ethanol conversion, butanol selectivity, butanol yield, and C$_{4+}$ alcohols selectivity significantly, while suppresses the DEE and ethylene selectivity.

Example 9

3 wt. % Palladium Catalysts on NH$_3$ Modified γ-Aluminum Oxide

The catalyst was synthesized using impregnation method. γ-Aluminum oxide was crushed to particle size of 0.85 mm and 1.18 mm. 10 g of the above crushed γ-aluminum oxide was placed in a round bottom reactor. 0.832 g of palladium (II) acetate was dissolved in 20 ml of acetone followed by the drop-wise addition of ammonium hydroxide with stirring until pH was adjusted to 12.5 and a clear solution was obtained. The palladium solution was impregnated to γ-aluminum oxide to obtain 3 wt. % palladium coated γ-aluminum oxide by stepwise incipient wetness using the rotating dryer. The palladium-coated γ-aluminum oxide was dried in the oven at 120° C. for 5 hours, followed by calcination using the following temperature program: start at 60° C., ramp to 350° C. at 2° C./min, hold at 350° C. for 5 hours, followed by cooling to room temperature.

Example 10

3 wt. % Cobalt Catalysts on NH₃ Modified γ-Aluminum Oxide

The catalyst was synthesized using impregnation method. γ-Aluminum oxide was crushed to particle size of 0.85 mm and 1.18 mm. 10 g of the above crushed γ-aluminum oxide was placed in a round bottom reactor. 1.53 g of cobalt nitrate hydrate was dissolved in 5 g of water, followed by the dropwise addition of ammonium hydroxide with stirring until pH was adjusted to 12.5 and a clear solution was obtained. The cobalt solution was impregnated to γ-aluminum oxide to obtain 3 wt. % cobalt coated γ-aluminum oxide by stepwise incipient wetness using the rotating dryer. The cobalt coated γ-aluminum oxide was dried in the oven at 120° C. for 5 hours, followed by calcination using the following temperature program: start at 60° C., ramp to 350° C. at 2° C./min, hold at 350° C. for 5 hours, followed by cooling to room temperature.

Comp. A—3 wt. % Palladium Catalysts on γ-Aluminum Oxide

The catalyst was synthesized using impregnation method. γ-Aluminum oxide was crushed to particle size of 0.85 mm and 1.18 mm. 10 g of the above crushed γ-aluminum oxide was placed in a round bottom reactor. 0.832 g of palladium (II) acetate was dissolved in 20 ml of acetone followed by impregnation to the γ-aluminum oxide by stepwise incipient wetness using the rotating dryer. The palladium-coated γ-aluminum oxide was dried in the oven at 120° C. for 5 hours, followed by calcination using the following temperature program: start at 60° C., ramp to 350° C. at 2° C./min, hold at 350° C. for 5 hours, followed by cooling to room temperature.

Comp. B—3 wt. % Cobalt Catalysts on γ-Aluminum Oxide

The catalyst was synthesized using impregnation method. γ-Aluminum oxide was crushed to particle size of 0.85 mm and 1.18 mm. 10 g of the above crushed γ-aluminum oxide was placed in a round bottom reactor. 1.53 g of cobalt nitrate hydrate was dissolved in 20 ml of acetone followed by impregnation to the γ-aluminum oxide by stepwise incipient wetness using the rotating dryer. The cobalt-coated γ-aluminum oxide was dried in the oven at 120° C. for 5 hours, followed by calcination using the following temperature program: start at 60° C., ramp to 350° C. at 2° C./min, hold at 350° C. for 5 hours, followed by cooling to room temperature.

Example 11

Table 4 compares two sets of catalysts. Example 9 is a palladium coated NH₃ modified γ-aluminum oxide catalyst and Example 10 is a cobalt coated NH₃ modified γ-aluminum oxide catalyst. As shown in Table 4, Example 9 has a similar ethanol conversion than the palladium coated unmodified γ-aluminum oxide catalyst. However, Examples 9 has a much greater butanol selectivity, butanol yield, $C_{4+}$ alcohols selectivity than the palladium coated unmodified γ-aluminum oxide catalyst. Furthermore, Example 9 dramatically reduced DEE selectivity from 51% to 8% and ethylene selectivity from 22% to 0%.

Example 10 also has better butanol selectivity, butanol yield, and $C_{4+}$ alcohols selectivity than the cobalt coated unmodified γ-aluminum oxide catalyst. Example 10 also dramatically reduced DEE selectivity from 60% to 8% and ethylene selectivity from 5% to 1%.

While the invention has been described in detail, modifications within the spirit and scope of the invention will be readily apparent to those of skill in the art. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the invention.

We claim:

1. A catalyst for converting alcohols to higher alcohols, the catalyst comprising:
    one or more metals selected from the group consisting of cobalt, palladium, and copper; and
    a support selected from the group consisting of γ-Aluminum Oxide, θ-Aluminum Oxide, and mixtures thereof;
    wherein the support has an average particle size ranging from 0.85 mm to 1.18 mm.

2. The catalyst of claim 1, wherein the one or more metals are present in an amount from 0.01 wt. % to 20 wt. %.

3. The catalyst of claim 1, wherein the support is present in an amount from 80 wt. % to 99.99 wt. %.

4. The catalyst of claim 1, further comprises a support modifier selected from the group consisting of pyridine, tetramethylammonium hydroxide, tetrabutylammonium hydroxide, ammonium hydroxide, methyl amine, and imidazole.

5. A catalyst for converting alcohols to higher alcohols, the catalyst comprising:

TABLE 4

Comparisons of NH₃ Modified γ-Aluminum Oxide Catalysts vs. Unmodified γ-Aluminum Oxide Catalysts
Testing condition: 290° C. and 5,100 kPa

| Catalysts | Ethanol Conversion (%) | Butanol Selectivity (%) | Yield (%) | $C_{4+}$ Alcohols Selectivity (%) | DEE Selectivity (%) | Ethylene Selectivity (%) |
|---|---|---|---|---|---|---|
| Example 9 | 40 | 54 | 22 | 75 | 8 | 0 |
| Comp. A | 39 | 6 | 2.3 | 12 | 51 | 22 |
| Example 10 | 55 | 51 | 28 | 73 | 8 | 1 |
| Comp. B | 80 | 3 | 2.4 | 6 | 60 | 5 | one or more supports selected from the group consisting of γ-Aluminum Oxide, θ-Aluminum Oxide, and mixtures thereof; and one or more metal layers on the one or more supports, wherein the one or more metal layers comprise one or more metals selected from the group consisting of cobalt, palladium, and copper;

wherein the support has an average particle size ranging from 0.85 mm to 1.18 mm.

6. The catalyst of claim 5, wherein the one or more metals are present in an amount from 0.01 wt. % to 20 wt. %.

7. The catalyst of claim 5, wherein the one or more supports are present in an amount from 80 wt. % to 99.99 wt. %.

8. A process for producing butanol, the process comprising the step of:

feeding a gaseous stream comprising ethanol over the catalyst of claim 5 in a reactor to form butanol.

9. A process for producing butanol, the process comprising the step of:

feeding a gaseous stream comprising ethanol over a catalyst in a reactor to form butanol, wherein the catalyst comprises one or more metals selected from the group consisting of cobalt, palladium, and copper; and one or more supports selected from the group consisting of γ-Aluminum Oxide, θ-Aluminum Oxide, and mixtures thereof;

wherein the support has an average particle size ranging from 0.85 mm to 1.18 mm.

10. The process of claim 9, wherein the reactor is operated at a temperature from 200° C. to 500° C.

11. The process of claim 9, wherein the reactor is operated at a pressure from 100 kPa to 20,000 kPa.

12. The process of claim 9, wherein ethanol conversion is at least 20%.

13. The process of claim 9, wherein butanol selectivity is at least 20%.

14. The process of claim 9, wherein ethylene selectivity is less than 10%.

15. The process of claim 9, wherein diethyl ether selectivity is less than 15%.

16. The process of claim 9, wherein the one or more metals are present in an amount from 0.01 wt. % to 20 wt. %, and the one or more supports are present in an amount from 80 wt. % to 99.99 wt. %.

17. The process of claim 9, wherein the gaseous stream is substantially free of hydrogen.

18. The process of claim 9, wherein the catalyst is substantially free of alkali metals and alkaline earth metals.

19. A catalyst for converting alcohols to higher alcohols, the catalyst comprising:

from 0.01 wt. % to 20 wt. % of one or more metals selected from the group consisting of palladium, platinum, tin, and copper; and a zirconium oxide support;

wherein the support has an average particle size ranging from 0.85 mm to 1.18 mm.

20. A process for producing butanol, the process comprising the step of:

feeding a gaseous stream comprising ethanol over the catalyst of claim 19 in a reactor to form butanol.

* * * * *